United States Patent [19]

Hirshorn et al.

[11] 4,408,604
[45] Oct. 11, 1983

[54] POROUS PACEMAKER ELECTRODE TIP

[75] Inventors: Michael S. Hirshorn, Double Bay; Michael Skalsky, Waverley, both of Australia; Petrus A. van Berkum, Elmhurst, Ill.; Loraine K. Holley, Rockdale; David K. Money, Pennant Hills, both of Australia

[73] Assignee: Teletronics Pty, Limited, New South Wales, Australia

[21] Appl. No.: 251,708

[22] Filed: Apr. 6, 1981

[51] Int. Cl.³ .............................................. A61N 1/04
[52] U.S. Cl. ................................. 128/785; 128/419 P
[58] Field of Search ............................... 128/784–786, 128/419 P

[56] References Cited

U.S. PATENT DOCUMENTS

| 3,754,555 | 8/1973 | Schmitt | 128/785 |
|---|---|---|---|
| 3,911,928 | 10/1975 | Lagergren | 128/418 |
| 3,935,864 | 2/1976 | Lagergren | 128/418 |
| 3,981,309 | 9/1976 | Cannon | 128/786 X |
| 4,011,861 | 3/1977 | Enger | 128/2.06 |
| 4,030,508 | 6/1977 | Thalen | 128/786 |
| 4,052,754 | 10/1977 | Homsy | 3/1.9 |
| 4,280,514 | 7/1981 | MacGregor | 128/786 |

FOREIGN PATENT DOCUMENTS

| 4967 | 10/1979 | European Pat. Off. . |
| 1471488 | 4/1977 | United Kingdom . |
| 2040685A | 9/1980 | United Kingdom . |
| 2065478A | 7/1981 | United Kingdom . |
| 2072514A | 10/1981 | United Kingdom . |

OTHER PUBLICATIONS

Munde et al., "Development of a Non-Polarizable Stimulating Electrode for Implantable Cardiac Pacemakers," Siemens Prosche u Entwicki-Ber BD 8 (1979) Nr4, pp. 227–234.

Hirshorn et al., "Histological Evaluation of Porous Titanium Cardiac Pacemaker Electrode Tips," First Asian-Pacific Symposium on Cardiac Pacing, Jun. 16, 1980, P2.37.

MacGregor et al., "The Porous-Surfaced Electrode," The Journal of Thoracic and Cardiovascular Surgery, vol. 38, No. 2, Aug. 1979 pp. 280-291.

Amundson et al., "The Porous Endocardial Electrode," PACE, vol. 2, Jan.-Feb. 1979, pp. 40-50.

Amundson, "Characteristics of the CPI Porous Tip Electrode," Impulse, Apr. 1979, pp. 7-10, 14.

Barold et al., "Cardiovascular Instrumentation," Chest, 70, Dec. 6, 1976, pp. 760-766.

Primary Examiner—Lee S. Cohen
Attorney, Agent, or Firm—Finnegan, Henderson, Farabow, garrett & Dunner

[57] ABSTRACT

A porous cardiac pacemaker electrode comprising a concavo-convex electrode cap having a plurality of apertures therethrough and an electrode shaft having a supporting edge formed thereon to which the concave surface of the electrode cap is joined. The porous cardiac pacemaker electrode is produced by deforming a platinum plate into a concavo-convex shaped cap member, forming a plurality of selectively spaced apertures through the electrode cap member to make the electrode cap substantially porous, forming an electrode shaft having a supporting edge, and joining the supporting edge of the electrode shaft to the concave surface of the electrode cap member.

12 Claims, 9 Drawing Figures

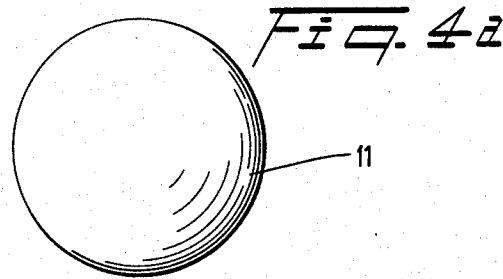
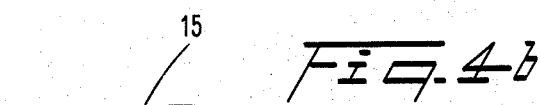
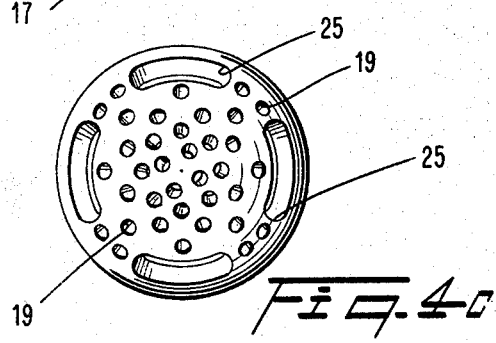
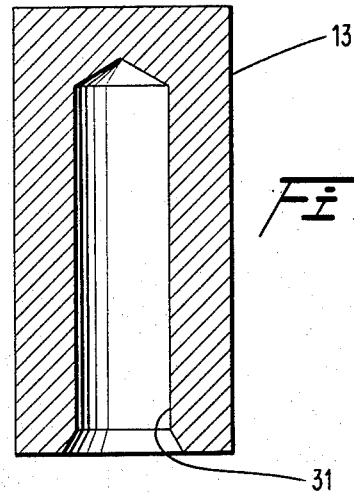
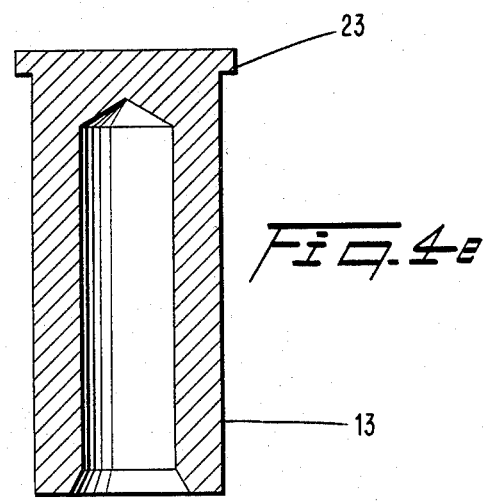
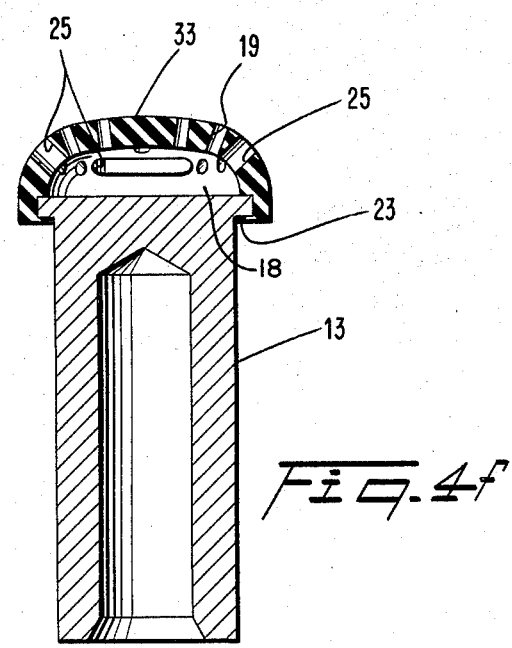

POROUS PACEMAKER ELECTRODE TIP

FIELD OF THE INVENTION

This invention relates with particularity to a porous electrode tip for use in a cardiac pacemaker and a method for making the electrode tip.

BACKGROUND OF THE INVENTION

Recently, the implantation of sophisticated electronic devices has become a routine procedure in many therapeutic procedures. Today cerebellar, bladder, peroneal nerve, and spinal cord stimulator, as well as cardiac pacemaker, implants are commercially available. Cochlear implants and other devices are in the development stage and will be useful treatment devices in the future.

Although these devices are used in various organs of the body, the applications have many elements in common. Each implantable device requires a signal generating system and a signal delivery system. In order to design a reliable, safe therapeutic device with a long life span for any of these applications, an understanding of the electrode-tissue interface is essential.

The main factors to be considered with regard to implantable electrodes are their constituent material, size and shape, the electrolyte composition, the system electrochemistry, and the tissue reaction. Each design factor must be tailored to meet the requirements of the application. For example, when implanting a cardiac pacemaker electrode, a degree of imprecision in the location of the electrode is tolerable, whereas difficulties in fixation of the implant are extremely undesirable. With cochlear implants, the electrode is easily fixed into place but the range of tolerance for positioning is extremely narrow.

The electronic design of an implantable stimulation apparatus is influenced by the optimum signal for tissue stimulation. In the case of a cardiac pacemaker, implant lifetime is determined by the energy delivered per pulse, and the pacemaker will have a longer life if the energy delivered per pulse is maintained at a minimum.

In physiological terms, the cardiac pacemaker must be capable of generating a signal with a sufficient magnitude to depolarize the excitable cells. The electrode size and shape, the electrolyte conductivity, and the distance separating the electrode and the excitable tissue determine the energy required of the pacemaker.

Over the last few years platinum and platinum in combination with iridium have become the most widely used cardiac pacemaker electrode materials, and have been accepted by regulatory bodies. Gold, stainless steel, palladium, silver, titanium, carbon, and tantalum have also been used in experimental applications.

In order to evaluate the suitability of an electrode system for each application, the impedance of the system to signals of differing frequencies must be known. In the case of a pacemaker, the current drain, and therefore the implant lifetime, is determined by the impedance to pacing pulses. The pacemaker electrode must not only deliver a pacing pulse with a pulse width in the range of 0.1-2.0 msec. to the tissue, but must also transmit a QRS signal (50 Hz) to the pacer circuitry. The pacemaker pulse is inhibited when normal ventricular depolarizations occur. The electrode-electrolyte system impedance is higher for sensing than for pacing. Electrodes are also used for pacing and sensing in the atrium which exhibits different stimulation and depolarization parameters than those of the ventricle.

The electrode/tissue system impedance characteristics may be understood in terms of an interface component which is the dominant component and occurs within one micron of the surface of the electrode, and a spreading resistance which depends predominantly on the tissue resistivity. The former reflects the charge transfer characteristics of the interface, and the latter reflects the size and shape of the electrode and the resistivity of the tissue.

The magnitude of the electrode/electrolyte impedance is frequency dependent because of the polarization effects at the interface with the surrounding tissue. At low frequencies, the interface impedance is significant.

The current drain of a pacemaker is determined by the impedance of the pacemaker circuitry, the nature of the electrode lead resistance, and the characteristics of the electrode tip interface with the electrolyte system. Since for a given pacemaker circuit and electrode lead design the current drain is well defined, the nature of the electrode tip/tissue interface determines the overall current requirements of the system. The most significant frequency of the pacing pulse is in the order of 1 KHz. At this frequency, the interface impedance is small and most of the impedance to the pacing pulses is due to the bulk or spreading impedance. This is determined by the shape of the electrode tip and is inversely related to the radius of the electrode tip.

The pacing impedance is indicative of the geometric surface area of the electrode tip and is a function of the electrode radius. For example, a hemispherical electrode tip having a small radius will have a higher pacing impedance and smaller current drain than a similarly shaped electrode tip of larger radius.

The most significant frequency components of a signal to be sensed, i.e., the ventricular QRS, are in the bandwidth of 20-100 Hz. In this region, the interface impedance becomes most significant. The interface impedance is determined by the microsurface area of the electrode tip and develops within a few microns of the surface. The microsurface area of an electrode tip is the area which includes all of the ridges, crevices, and indentations in the surface of the electrode tip.

It has been determined that the pacing threshold is a reflection of the energy required for a pulse to initiate a cardiac contraction. The stimulation threshold rises for weeks after the implant of a cardiac pacemaker as a result of an increase in the spacing between the electrode and the excitable tissue. The increase occurs due to the development of a fibrous capsule around the electrode tip which is reported to be between 0.3 mm and 3 mm thick.

In view of the above characteristics of an electrode for a cardiac pacemaker, it is clear that an electrode tip with a small geometric surface area and high pacing impedance will have a low current drain. However, in order to enhance sensing, the same electrode tip should have a large microsurface area to result in a low sensing impedance. Although this combination of characteristics seems to be incompatible, it has been obtained in a cardiac pacemaker electrode tip that is constructed to be porous. One such porous electrode tip comprises a platinum-iridium screen covering a mesh ball of the same alloy.

One of the advantages of a porous electrode tip is the ability to minimize the radius of the electrode tip to present a small geometric surface area while having an increased aggregate microsurface area. This extends the lifetime of the pacemaker by providing a high pacing impedance and a lower current drain. On the other hand, a large microsurface area is provided by virtue of the mesh-like construction. The large microsurface area enables enhanced sensing by lowering the sensing impedance.

It has been found, however, that a mesh-like construction presents difficulties in fabricating the porous electrode tip. These include the control over the shaping and the bonding of the mesh in a precise manner. These attributes are necessary to make certain that the porous electrode tip will exhibit uniform impedance and other electrical properties as well as sufficient reliability of construction.

Thus, there has been a need to provide a cardiac pacemaker porous electrode tip which is easier to make in appropriate shapes, has predictable, predetermined electrical properties, and is of adequate reliability.

An area of vital importance that is often not considered in detail is the tissue reaction to the electrode itself. Biocompatibility is a term often used to describe the general suitability of a material for implantation. Generalizations concerning this term are of little practical value because each implant application has different tissue reaction requirements. Systemic toxicity is of course undesirable, however, fibrous reaction may be useful for prosthesis attachment. In the case of a pacemaker electrode, minimal tissue reaction is desired around the tip but firm attachment of the electrode to the tissue is essential.

A porous electrode tip allows rapid fibrous tissue growth into a hollow area or cavity in the electrode tip itself to enhance attachment of the electrode to the heart. A smaller dislodgement rate is expected as a result of such tissue ingrowth.

A further aspect of importance is selection of pore size, which must be such as to accommodate economical construction techniques, overall dimensional tolerances, and tissue response constraints. Any design must balance the pore size, the number of pores, the pore intercommunications, and mechanical stability. Recent research has suggested that the selection of pore size has an influence on the tissue reaction to porous materials. Although this area is in its infancy, it is clear that pore diameter should be at least 15 microns to allow tissue ingrowth. It has also been suggested that pore size will determine tissue capsule thickness and, thus, stimulation threshold.

From the above discussion, it is clear that an ideal porous electrode tip construction should allow precise selection of pore size and pore configuration. The invention to be described provides a clear improvement over the prior art in this regard.

The present invention allows the independent variation of porosity and microsurface area. The pore size may be selected on the basis of optimal tissue ingrowth and attachment with minimal chronic tissue thickness. The high microsurface area decreases the sensing impedance and is determined predominantly by the roughening process. Theoretical studies and laboratory experiments have shown that with the pore size selected, the internal cap surface, which defines an internal cavity, does not make a major contribution to the reduction of sensing impedance.

The importance of distinguishing between calculated and available microsurface area for sensing is not stated in the literature relating to the prior art. The embodiment to be described hereinafter takes advantage of the microsurface area of a roughened external surface as well as the surface area of the cap. The roughening process is critical to the achievement of sufficiently low sensing impedance and this development gives rise to improved porous electrode design and construction possibilities.

Additional objects and advantages of the invention will be set forth in part in the description which follows, and in part will be apparent from the description or may be learned from the practice of the invention. The objects and advantages of the invention may be realized and obtained by means of the instrumentalities and combinations particularly pointed out in the appended claims.

SUMMARY OF THE INVENTION

It is accordingly an object of the present invention to improve porous cardiac pacemaker electrode tips.

A further object of this invention is to design an improved porous cardiac pacemaker electrode tip which exhibits electrical properties within a narrow and accurately definable range.

It is yet another object of this invention to provide an improved porous cardiac pacemaker electrode tip having a small geometric surface area and high pacing impedance as well as a large microsurface area and low sensing impedance.

A further object of this invention is to produce improved porous cardiac pacemaker electrode tips which will remain mechanically intact after years of implantation within a body.

To achieve the foregoing objects in accordance with the invention, as embodied and broadly described herein, a porous electrode for use in a cardiac pacemaker comprises a cap having a plurality of apertures therethrough extending from the external surface to the internal surface thereof, and an electrode shaft being joined to the cap and an internal cavity defined by the inner surface of the cap.

The porous electrode is formed by a method comprising the steps of forming an electrode cap, which together with a top of an electrode shaft forms a cavity, forming a plurality of apertures through the electrode cap to make the electrode cap substantially porous, forming an electrode shaft, joining the electrode shaft to the electrode cap, and increasing the microsurface area of the cap.

BRIEF DESCRIPTION OF THE DRAWINGS

The manner in which the apparatus of the present invention is constructed and the inventive method for forming the apparatus of the present invention can best be understood in light of the following detailed description, together with the accompanying drawings, in which:

FIGS. 4(a)–4(f) illustrate the steps performed in the method for constructing the porous cardiac pacemaker electrode tip of FIG. 1.

DETAILED DESCRIPTION OF THE PREFERRED EMBODIMENT

Figure 1:
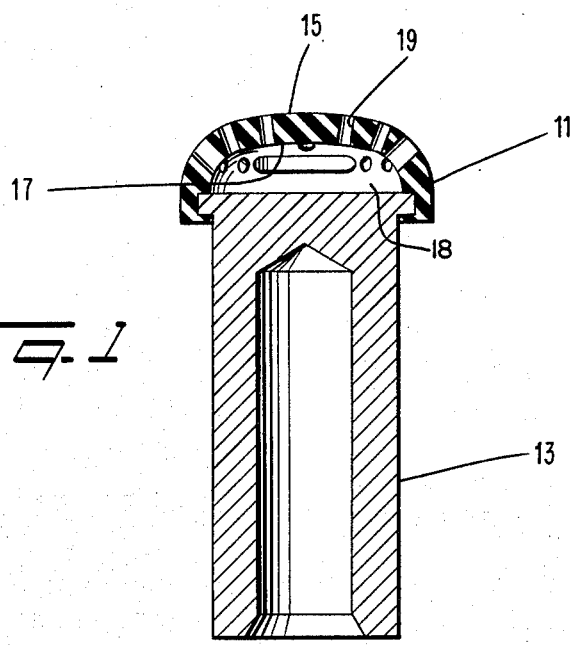
FIG. 1 is a cross-sectional view of the cardiac pacemaker porous electrode tip of the instant invention.

Referring to FIG. 1, the cardiac pacemaker porous electrode tip of the instant invention comprises an electrode cap 11 and an electrode shaft 13. The electrode cap 11 comprises, for example, a 0.25 mm thick section of platinum sheet or rod which has been formed into a substantially concavo-convex shape having an area in the range of 4 mm$^2$ to 8 mm$^2$ and a diameter of approximately 2 mm. The convex surface 15 comprises the exterior surface of the electrode cap 11 and defines a hollow area or cavity 18 above the end of the electrode shaft 13 and the concave surface 17 comprises the interior surface of the electrode cap 11.

A plurality of apertures 19 (FIG. 3) is drilled through the electrode cap 11 to communicate with the cavity 18. In the preferred embodiment the apertures 19 are provided in a uniformly spaced manner. Also, in the preferred embodiment, there are at least 55 of the apertures 19 of a generally circular cross section and having interior diameters in the range of 15 to 300 microns. Alternatively the apertures 19 are generally frusto-conical shape having an interior diameter of 120 microns in the convex surface 15 and an interior diameter of 100 microns at the concave surface 17. There are also four equally-spaced apertures 25 of generally oval shape with a major diameter of approximately 900 microns and a minor diameter of approximately 120 microns located near the peripheral rim of the cap 11. These larger apertures 25 facilitate fluid ingress and tissue ingrowth in the case of "side on" electrode tip location. It is contemplated, however, that the diameters of the apertures could be varied or that the apertures could be formed in different geometrical shapes. For example the major diameters of the apertures 25 could be in the range of 60 to 1200 microns and the minor diameters could be in the range of 15 to 300 microns.

Figure 2:
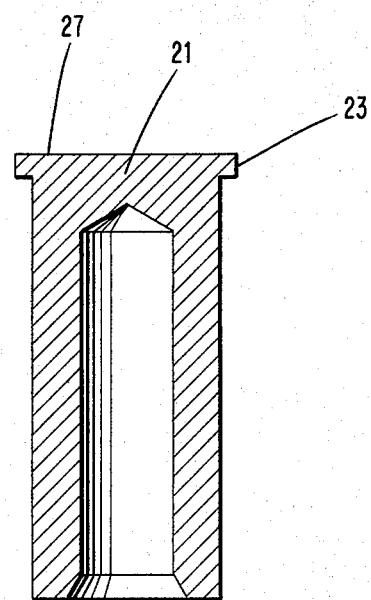
FIG. 2 is a cross-sectional view of the shaft for the electrode tip of FIG. 1.

As shown in FIG. 2, one end 27 of the cylindrical member 21 has been constructed with a supporting edge 23. The other end 29 of the cylindrical member 21 interfaces with the electrical conductor used in the pacemaker lead.

Figure 3:
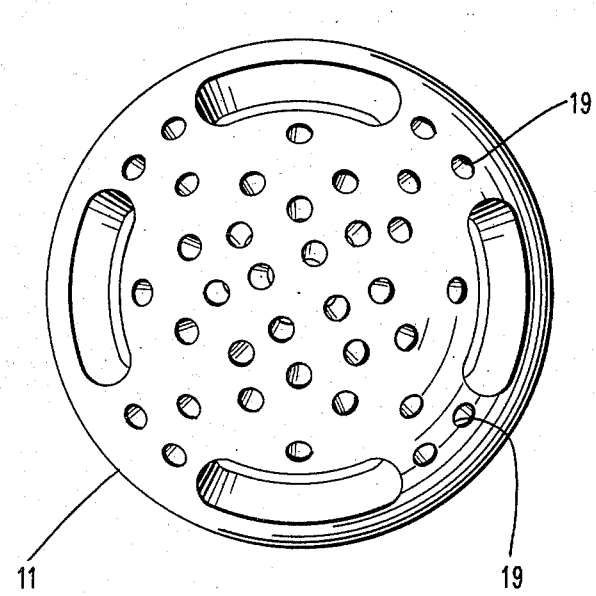
FIG. 3 is a top view of the cardiac pacemaker electrode tip of FIG. 1.

FIG. 3 is a top view of the electrode cap 11 and illustrates the location of the apertures in the electrode cap 11.

The geometric surface area of the electrode cap 11 is approximately 8.0 mm$^2$. This small area results in an increased pacing impedance. When considering the interior surfaces of the apertures 19 and 25 extending through the electrode cap 11, the internal surface 15 of the cap 11, and the external surface 17 of the cap 11, the microsurface area of the entire electrode cap 11 is approximately 20 mm$^2$.

FIGS. 4(a)-4(f) illustrate an example of the step to be performed during the fabrication of a porous cardiac pacemaker electrode of the instant invention. First, as illustrated in FIG. 4(a), a plate of platinum or other suitable electrode material is provided.

The platinum plate is deformed or machined to a substantially concavo-convex shape as illustrated in FIG. 4(b). Next, a plurality of apertures 19 and 25 are formed in the concavo-convex plate as illustrated in FIG. 4(c). It is contemplated that the aperture-forming step will be performed by drilling with a laser, electron beam device, or other means capable of drilling apertures of predetermined shapes and sizes in an accurately locatable manner. Moreover, the location and number of the apertures 19, 25 will be selected according to the desired electrical properties for the electrode and the desired extent of tissue ingrowth.

As shown in FIG. 4(d), an electrode shaft 13 is provided with an opening 31 to accommodate an electrode conductor lead (not shown). Next, the end of the electrode shaft 13 is treated to provide the supporting edge 23 as shown in FIG. 4(e). Finally, as illustrated in FIG. 4(f), the supporting edge 23 is joined to the concave surface 17 of the electrode cap 11 by means of laser welding or other equivalent treatment.

The external surface 15 of the cap 11 then has its microsurface area increased by roughening to form at least one area 33 (FIG. 4(f)) with crevices, irregularities, protuberances, etc. thereon. The preferred method of roughening the exterior surface 15 of the cap 11 is by glass bead blasting. Nonetheless, methods such as spark erosion (electrical needle etching), could be used. A suitable roughening method is disclosed in U.S. patent application Ser. No. 251,340 filed on even date herewith on behalf of Hirshorn et al. and entitled "Cardiac Pacemaker Electrode Tip Structure And Methods For Making the Same". The disclosure of that application is incorporated herein by reference.

The above-described method produces a porous cardiac pacemaker electrode having a small geometric surface area, and thus, a high pacing impedance to ensure a low current drain on the pacemaker power source. Simultaneously, the design provides a large microsurface area enabling a low sensing impedance and improved sensing capability. Also, the plurality of apertures through the electrode, which causes it to be porous, facilitates the attachment of the electrode to the surrounding tissue by enabling the tissue to grow into the apertures and minimize the chronic tissue capsule thickness and consequent threshold.

It will be apparent, to those skilled in the art, that modifications and variations can be made in the preferred embodiment disclosed herein and in the method of constructing the preferred embodiment without departing from the scope or the spirit of the invention. Thus, it is intended that the present invention include those modifications and variations which come within the scope of the appended claims and their equivalents.

What is claimed is:

1. An implantable porous electrode for use in a cardiac pacemaker comprising:
   an electrode cap having an inner surface, an outer surface, and a plurality of uniformly spaced apertures extending from said inner surface through said electrode cap to said outer surface, and adapted for tissue ingrowth when the electrode is implanted; and
   an electrode shaft joined to said cap with a cavity resulting between said inner surface of said cap and said shaft.

2. A porous electrode according to claim 1 wherein said electrode cap and said electrode shaft are formed of platinum.

3. A porous electrode according to claim 1 wherein said electrode cap is formed in a concavo-convex shape.

4. A porous electrode according to claim 1 wherein said electrode shaft includes a supporting edge and wherein said electrode cap is joined to said supporting edge.

5. A porous electrode according to claim 1, 2, 3, or 4 wherein said apertures formed through said electrode cap are substantially circular and of uniform size with diameters in the range of 15 to 300 microns.

6. A porous electrode according to claim 5 further including a second plurality of apertures substantially oval in cross section and uniform in size, with major diameters in the range of 60 to 1200 microns and minor diameters in the range of 15 to 300 microns.

7. A porous electrode according to claim 6 further including at least one roughened area on said outer surface of said cap to increase the microsurface area of said cap.

8. A porous electrode according to claim 1, 2, 3, or 4 wherein said apertures in said cap are of a substantially oval cross section and are uniform in size, with major diameters in the range of 60 to 1200 microns and minor diameters in the range of 15 to 300 microns.

9. A porous electrode according to claim 1, 2, 3, or 4 wherein the said electrode cap has a geometric area of at least 4 mm$^2$.

10. A porous electrode according to claim 1, 2, 3, or 4 further including at least one roughened area on said outer surface of said cap to increase the microsurface area of said cap.

11. A porous electrode according to claim 10 wherein said electrode cap has a geometric area greater than 4 mm$^2$.

12. A porous electrode according to claim 11 having a cap diameter of at least 2 mm.

* * * * *